United States Patent
Marnfeldt et al.

(10) Patent No.: US 10,004,911 B2
(45) Date of Patent: Jun. 26, 2018

(54) CIRCUITRY FOR CHARGING A DEPLETED BATTERY IN AN IMPLANTABLE MEDICAL DEVICE WITHOUT PASSIVE TRICKLE CHARGING

(71) Applicant: Boston Scientific Neuromodulation Corporation, Valencia, CA (US)

(72) Inventors: Goran N. Marnfeldt, Valencia, CA (US); Rafael Carbunaru, Valley Village, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 409 days.

(21) Appl. No.: 14/593,669

(22) Filed: Jan. 9, 2015

(65) Prior Publication Data
US 2015/0196768 A1  Jul. 16, 2015

Related U.S. Application Data
(60) Provisional application No. 61/928,342, filed on Jan. 16, 2014.

(51) Int. Cl.
*A61N 1/378* (2006.01)
*A61N 1/36* (2006.01)
(Continued)

(52) U.S. Cl.
CPC ....... *A61N 1/3787* (2013.01); *A61N 1/36125* (2013.01); *H02J 7/0073* (2013.01);
(Continued)

(58) Field of Classification Search
CPC .................................................. A61N 1/3787
See application file for complete search history.

(56) References Cited

U.S. PATENT DOCUMENTS 6,020,778 A   2/2000 Shigehara et al.
6,516,227 B1  2/2003 Meadows et al.
(Continued)

FOREIGN PATENT DOCUMENTS

JP       8-103034         4/1996
WO   WO2013/012487    *  1/2013

OTHER PUBLICATIONS

International Search Report and Written Opinion regarding corresponding PCT Application No. PCT/US2015/011001, dated Mar. 31, 2015.
(Continued)

*Primary Examiner* — Carl H Layno
*Assistant Examiner* — Jennifer Ghand
(74) *Attorney, Agent, or Firm* — Lewis, Reese & Nesmith, PLLC (57) ABSTRACT

Charging circuitry is disclosed for receiving a magnetic charging field and using the received field to charge a battery in an Implantable Medical Device (IMD) without passive trickle charging, and even if the battery voltage (Vbat) is severely depleted. The charging circuitry includes a source capable of producing a constant charging current via a current mirror that receives a reference current for setting the charging current. Two reference current generators are provided: a first enabled when Vbat is severely depleted to produce a small non-adjustable reference current; and a second enabled once Vbat is recovered to produce a reference current that can be controlled to adjust the charging current. Because Vbat may be too low, the first generator is powered by a DC voltage produced from the magnetic charging field. A passively-generated undervoltage control signal is used to transition between use of the first and second generators.

25 Claims, 7 Drawing Sheets

(51) Int. Cl.
  *H02J 7/00* (2006.01)
  *H02J 7/02* (2016.01)
  *H02J 5/00* (2016.01)
  *A61N 1/37* (2006.01)
  *H02J 7/04* (2006.01)

(52) U.S. Cl.
  CPC .............. *H02J 7/0077* (2013.01); *H02J 7/02* (2013.01); *A61N 1/3708* (2013.01); *H02J 5/005* (2013.01); *H02J 7/025* (2013.01); *H02J 7/045* (2013.01)

(56) References Cited

U.S. PATENT DOCUMENTS

| | | |
|---|---|---|
| 7,177,698 B2 | 2/2007 | Klosterman et al. |
| 7,962,222 B2 | 6/2011 | He et al. |
| 8,649,858 B2 | 2/2014 | Griffith et al. |
| 8,666,504 B2 | 3/2014 | Dronov et al. |
| 8,744,592 B2 | 6/2014 | Carbunaru et al. |
| 8,781,596 B2 | 7/2014 | Aghassian et al. |
| 2006/0152194 A1 | 7/2006 | Wang et al. |
| 2007/0150019 A1 | 6/2007 | Youker et al. |
| 2011/0204855 A1 | 8/2011 | LoCascio |
| 2012/0095529 A1 | 4/2012 | Parramon et al. |
| 2013/0023943 A1 | 1/2013 | Parramon et al. |
| 2013/0096651 A1 | 4/2013 | Ozawa et al. |
| 2014/0249603 A1 | 9/2014 | Yan et al. |

OTHER PUBLICATIONS

U.S. Appl. No. 61/877,871, filed Sep. 13, 2013, Funderburk.
Notification of Reason for Rejection regarding corresponding Japanese patent application No. 2016-565096, dated Apr. 12, 2017.

\* cited by examiner

CIRCUITRY FOR CHARGING A DEPLETED BATTERY IN AN IMPLANTABLE MEDICAL DEVICE WITHOUT PASSIVE TRICKLE CHARGING

CROSS REFERENCE TO RELATED APPLICATIONS

This is a non-provisional of U.S. provisional patent application Ser. No. 61/928,342, filed Jan. 16, 2014, which is incorporated herein by reference, and to which priority is claimed.

This application is related to U.S. provisional patent applications 61/928,352 and 61/928,391, both filed Jan. 16, 2014, which are both incorporated herein by reference in their entireties.

FIELD OF THE INVENTION

This application relates to the field of implantable medical devices, and in particular to battery charging circuitry for an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

Figure 1A:
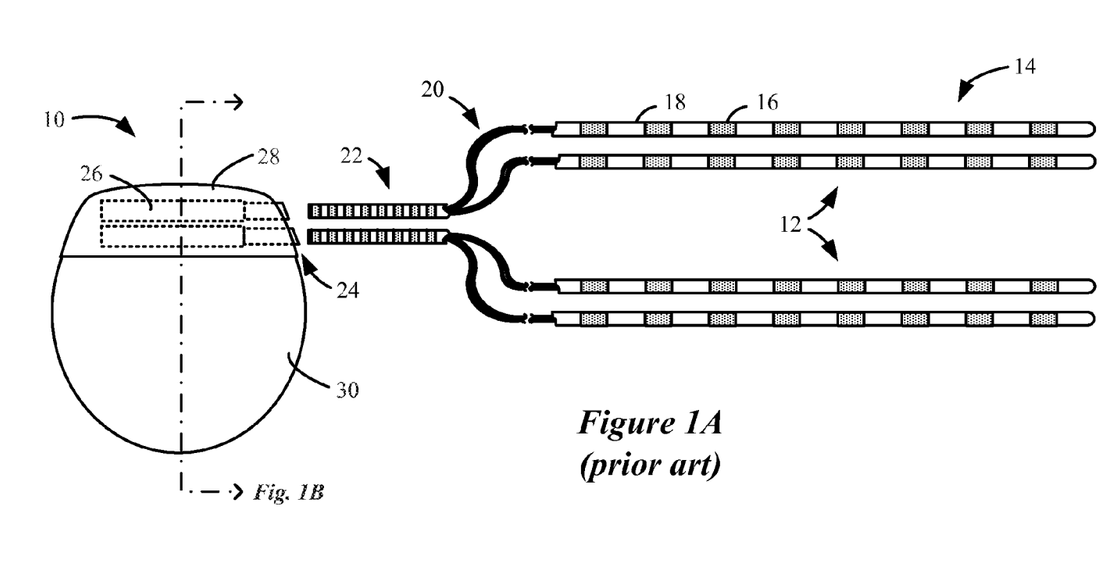
FIGS. 1A and 1B show a rechargeable battery implantable pulse generator (IPG) in plan and cross sectional views, in accordance with the prior art.
Figure 1B:
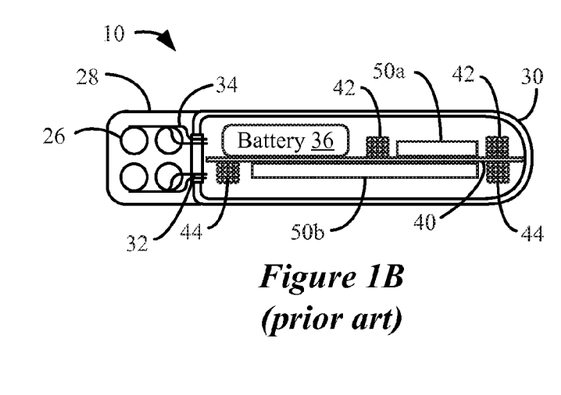

An SCS system typically includes an Implantable Pulse Generator (IPG) 10 shown in plan and cross-sectional views in FIGS. 1A and 1B. The IPG 10 includes a biocompatible device case 30 that holds the circuitry and battery 36 necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26, which are in turn coupled by feedthrough pins 34 through a case feedthrough 32 to circuitry within the case 30.

In the illustrated IPG 10, there are thirty-two lead electrodes (E1-E32) split between four leads 14, with the header 28 containing a 2×2 array of lead connectors 24. However, the number of leads and electrodes in an IPG is application specific and therefore can vary. In a SCS application, the electrode leads 14 are typically implanted proximate to the dura in a patient's spinal cord, and when a four-lead IPG 10 is used, these leads are usually split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IPG 10 can also be used for Deep Brain Stimulation (DBS) in another example. In other IPG examples designed for implantation directly at a site requiring stimulation, the IPG can be lead-less, having electrodes 16 instead appearing on the body of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 50a and 50b coupled to top and bottom surfaces of the PCB; a telemetry coil 42 for wirelessly communicating with an external controller (not shown); a charging coil 44 for wirelessly receiving a magnetic charging field from an external charger 90 (FIG. 2) for recharging the battery 36; and the feedthrough pins 34 (connection not shown). If battery 36 is permanent and not rechargeable, charging coil 44 would be unnecessary. (Further details concerning operation of the coils 42 and 44 and the external devices with which they communicate can be found in U.S. Patent Application Ser. No. 61/877,871, filed Sep. 13, 2013).

Figure 2:
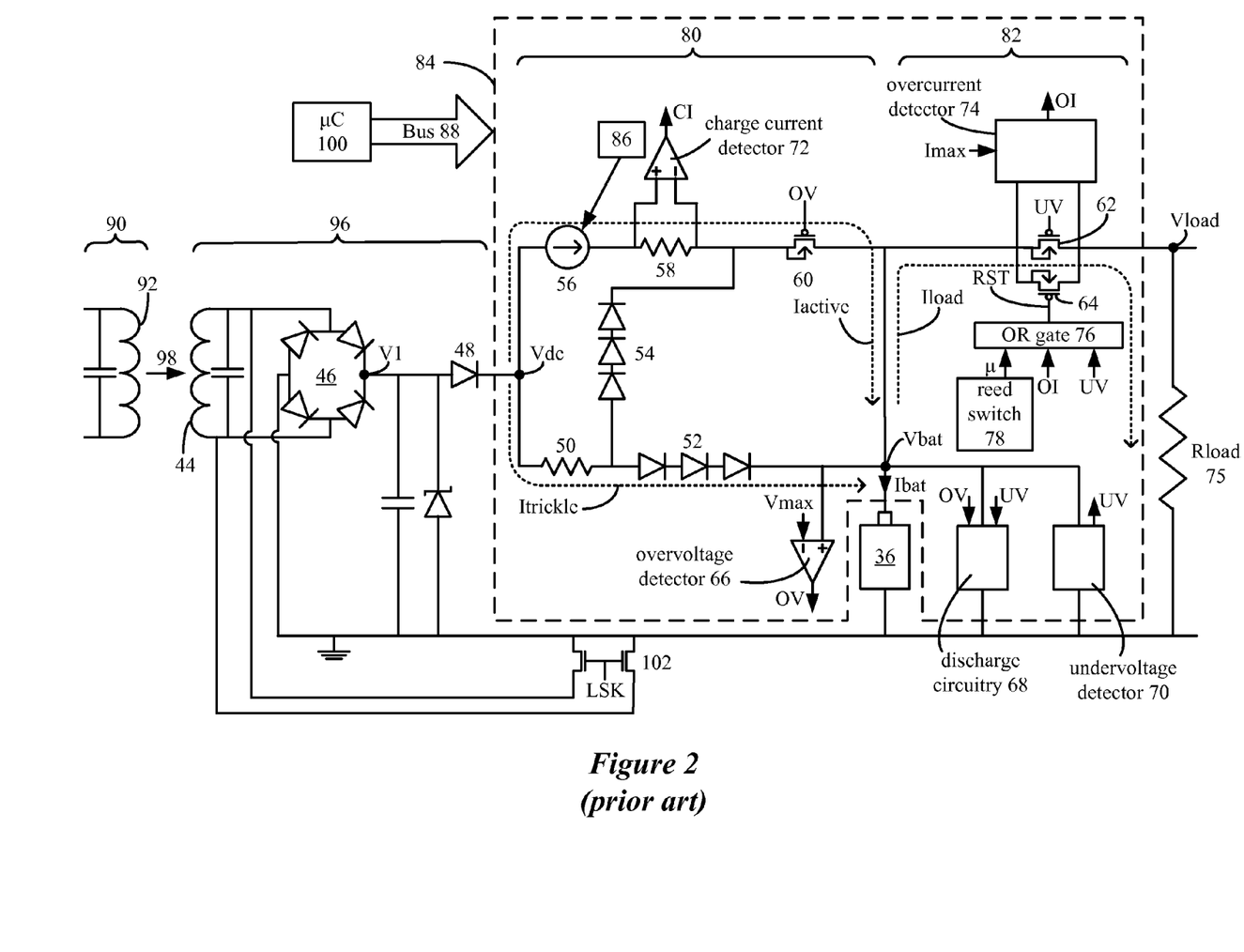
FIG. 2 shows battery management circuitry for an IPG including both trickle and active charging paths, in accordance with the prior art.

An issue requiring care in an IPG 10, especially one in which the battery 36 is rechargeable, is design of the battery management circuitry, which is described in one example in commonly-owned U.S. Patent Application Publication 2013/0023943, which is incorporated herein by reference in its entirety. FIG. 2 shows the battery management circuitry 84 disclosed in the '943 Publication, which is briefly discussed. Rechargeable battery 36 may comprise a Li-ion polymer battery, which when fully charged can provide a voltage (Vbat=Vmax) of about 4.2 Volts. However, other rechargeable battery chemistries could be used for battery 36 as well.

As noted, an external charger 90, typically a hand-held, battery-powered device, produces a magnetic non-data modulated charging field 98 (e.g., 80 kHz) from a coil 92. The magnetic field 98 is met in the IPG 10 by front-end charging circuitry 96, where it energizes the charging coil 44 by inducing a current in the coil. The induced current is processed by rectifier circuitry 46, including a rectifier and optionally a filtering capacitor and a voltage-magnitude-limiting Zener diode, e.g., to 5.5V), to establish a voltage V1 (e.g., ≤5.5V), which voltage is passed through a back-flow-prevention diode 48 to produce a DC voltage, Vdc. Transistors 102 coupled to the charging coil 44 can be controlled by the IPG 10 (via control signal LSK) to transmit data back to the external charger 90 during production of the magnetic field 98 via Load Shift Keying, as is well known.

As discussed in the '943 Publication, Vdc is provided to battery management circuitry 84, which may reside on an Application Specific Integrated Circuit (ASIC) along with other circuitry necessary for IPG 10 operation, including current generation circuitry (used to provide specified currents to selected ones of the electrodes 16); telemetry circuitry (for modulating and demodulating data associated with telemetry coil 42 of FIG. 1B); various measurement and generator circuits; system memory; etc. The front-end charging circuitry 96 and the battery 36 typically comprise off-chip (off-ASIC) components, along with other electronics in the IPG 10, such as the telemetry coil 42; various DC-blocking capacitors coupled to the electrodes 16 (not shown); a microcontroller 100, which can communicate with the ASIC (and the battery management circuitry 84) via a digital bus 88; and other components of lesser relevance here. Microcontroller 100 may comprise in one example Part Number MSP430, manufactured by Texas Instruments, which is described in data sheets at http://www.ti.com/lsds/ti/microcontroller/16-bit_msp430/overview.page?DCMP=MCU_other& HQS=msp430, which is incorporated herein by reference. The ASIC may be as described in U.S. Patent Application Publication 2012/0095529, which is also incorporated herein by reference.

The battery management circuitry 84 in FIG. 2 is comprised of two circuit blocks: charging circuitry 80 for generating a current for charging the battery 36, and load isolation circuitry 82 for controllably connecting or disconnecting the battery 36 from the load 75 that the battery 36 powers during normal operation of the IPG 10. Load 75 can comprise both on-chip (on-ASIC) circuit blocks such as the current generation circuitry and the telemetry circuitry mentioned earlier, and off-chip (off-ASIC) components such as the microcontroller 100.

As depicted, the charging circuitry 80, the load isolation circuitry 82, and the battery 36 generally have a T-shaped topology, with the charging circuitry 80 intervening between front-end charging circuitry 96 (Vdc) and the positive terminal (Vbat) of the battery 36, and with the load isolation circuitry 82 intervening between Vbat and the load 75.

As discussed in the '943 Publication, the load isolation circuitry 82 can prohibit the battery 36 (Vbat) from being passed to power the load (Vload) dependent on a number of conditions. For example, if the load 75 is drawing a significantly high current (as indicated by overcurrent detection circuitry 74 via assertion of control signal OI), or if Vbat is too low (as indicated by undervoltage detection circuitry 70 via assertion of control signal UV), or if an external magnetic field signal μ, is indicated by a Reed switch 78 (e.g., in an emergency condition warranting presentation by the patient of an external shut-off magnet), the load 75 will be decoupled from Vbat via switches 62 or 64 as assisted by OR gate 76. Load isolation circuitry 82 is discussed in further detail in the above-incorporated '943 Publication. Discharge circuitry 68 is also provided to intentionally drain the battery 36 if Vbat is too high.

Of greater relevance to the present disclosure is the charging circuitry 80, which begins at Vdc—the DC-voltage produced by the front-end charging circuitry 96 in response to the external charger 90's magnetic field 98. Vdc splits into two paths in the charging circuitry 80 that are connected in parallel between Vdc and Vbat: a trickle charging path, and an active charging path, either of which can be used to provide a battery charging current (Ibat) to the battery 36 (Vbat).

The trickle charging path is passive, i.e., its operation is not controlled by control signals, and requires no power other than that provided by Vdc to produce a charging current (Itrickle) for the battery 36. As shown, the trickle charging path presents Vdc to a current-limiting resistor 50 and one or more diodes 52, and is used to provide a small charging current, Itrickle, to the battery 36. Using a small trickle charging current is particularly useful when the battery 36 is significantly depleted, i.e., if Vbat is below a threshold Vt1, such as 2.7V for example.

To produce Itrickle, Vdc must be higher than the sum of the voltage drops across the resistor 50 and diode(s) 52 and the voltage of the battery 36, Vbat. Under typical conditions and assuming three diodes 52 and a 200-ohm resistor 50 are used, the drop across the resistor 50 and diode(s) 52 will be about 2.0 Volts. Therefore, Itrickle will passively flow into the battery 36 if Vdc is greater than about 2.0V+Vbat. If this condition is not met—which would indicate that Vdc is too small (perhaps because the coupling between the external charger 90 and the IPG 10 is poor), or that Vbat is too high (which may occur as the battery 36 is gradually charged)—diodes 52 will prevent the battery 36 from draining backwards through the trickle charging path. Itrickle is generally on the order of ten milliamps. This is desirably small, because a significantly depleted rechargeable battery 36 can be damaged if it receives charging currents (Ibat) that are too high, as is well known.

The active charging path proceeds in FIG. 2 from Vdc to the battery 36 through current/voltage source circuitry 56, which is used to produce charging current Iactive. In the example of FIG. 2, the active charging path also passes through control and protective measures of the battery management circuitry 84, including a charging current sense resistor 58 used in conjunction with a charging current detector 72, and an overvoltage protection switch 60 used in conjunction with an overvoltage detector 66 to open circuit the active charging path if the battery voltage, Vbat, exceeds a maximum value (such as Vmax=4.2V).

Figure 3A:
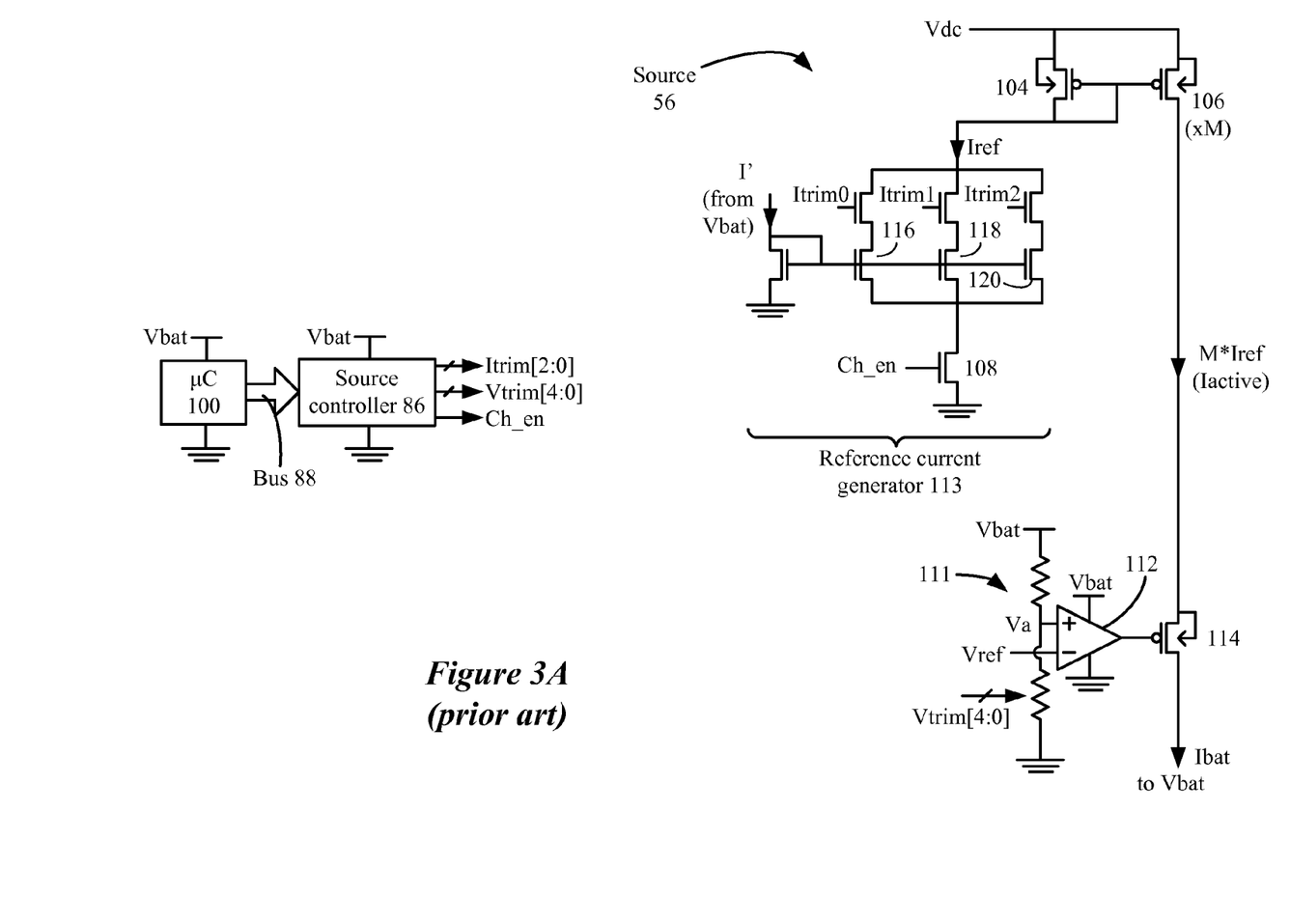

Circuitry for the current/voltage source 56 in the active charging path is shown in FIG. 3A. As its name implies, source 56 can be controlled to provide either a constant current or a constant voltage to the battery 36 during active charging. The source 56 comprises a current mirror comprised of P-channel transistors 104 and 106, which are powered by Vdc and receive a reference current, Iref, provided by reference current generator circuitry 113. Current mirror control transistor 104 mirrors a representation of Iref in current mirror output transistor(s) 106 to produce the active charging current, Iactive. In the example shown, M output transistors 106 are wired in parallel, and thus the current provided by output transistor(s) 106 equals Iactive=M*Iref. A single wider output transistor 106 (M times wider than the current mirror control transistor 104) could also be used.

The reference current generator 113 used to produce Iref is adjustable via one or more control signals Itrim[2:0], and also comprises a current mirror. As shown, a system reference current, I' (e.g., 100 nA), is mirrored transistors 116, 118, and 120, each of which are coupled in series to gating transistors controlled by the Itrim control signals. Transistors 116, 118, and 120 are preferably of different widths, or comprise different numbers of transistors in parallel, to provide different contributions to Iref. For example, transistors 116, 118, and 120 may respectively contribute I'*N, I'*2N, and I'*4N to Iref, thus allowing Iref to vary from I'*N to I'*7N in increments of I'*N, depending on which control signals Itrim0, Itrim1, and Itrim2 are active. Additional Itrim control signals and additional current mirror output transistors (e.g., 116-120) could be used to control Iref over a wider range, and/or with smaller resolution. Adjusting Iref in this manner in turn adjusts Iactive via operation of the current mirror transistor 104 and 106 discussed above.

Control signals Itrim are issued by a source controller 86, which communicates with the microcontroller 100 by a digital bus 88, and so the microcontroller 100 can control the source controller 86 to in turn control the source 56 via Itrim and other control signals discussed further below.

The mode in which the source 56 operates to generate a charging current depends on the magnitude of the battery voltage, Vbat, which is known to the microcontroller 100. If the battery 36 is significantly depleted, i.e., Vbat<Vt1 (e.g., 2.7), the microcontroller 100 commands the source controller 86 to disable the source 56. This occurs by the source controller 86 issuing charge enable control signal Ch_en='0' to the reference current generator 113, which turns off N-channel transistor 108 and disables generation of the reference current, Iref, and hence Iactive. Thus, the battery 36 in this circumstance can only be charged via the trickle charging path, and only if magnetic field 98 and Vdc are present and sufficient.

If Vbat>Vt1, but below an upper threshold Vt2 described further below (i.e., if Vt1<Vbat<Vt2), the source 56 operates in a constant current mode. In this mode, Ch_en='1', and transistor 108 allows Iref and hence Iactive to flow with a magnitude ultimately set by the Itrim control signals. When source 56 operates in constant current mode, Iactive is generally on the order of 50 milliamps. A P-channel transistor switch 114 in the active current path is fully on in constant current mode, thus allowing Iactive to flow from the source 56 to the battery 36 without resistance.

If Vbat>Vt2 (e.g., 4.0 V), the source 56 operates in a constant voltage mode. Ch_en and the Itrim control signals are still asserted in this mode. Crossing of the Vt2 threshold and switching of charging modes does not in this example rely on the microcontroller 100, but is instead affected via Vbat measurement circuitry 111 in the source 56. Vbat is determined in this circuitry 111 via a high-impedance resistor ladder, which produces a voltage Va indicative of Vbat. Va and a known band-gap reference voltage, Vref, are compared at amplifier 112. When Va>Vref, indicating that Vbat>Vt2, the amplifier 112 starts to turn off transistor 114, and the source 56 operates in constant voltage mode, providing an essentially constant voltage to the positive terminal of the battery 36. As the internal cell voltage of the battery 36 increases in this mode, its internal resistance causes Iactive to fall off exponentially, until Vbat reaches a maximum value, Vmax (e.g., 4.2V). At this point, the microcontroller 100 will consider charging of the battery 36 to be complete, and will once again assert Ch_en='0' to curtail further active charging. (Additionally, overvoltage switch 60 may also be opened). By contrast, when Va<Vref, indicating that Vbat<Vt2, the amplifier 112 turns on P-channel transistor 114, and the source 56 operates in constant current mode as described earlier. Voltage Va can be trimmed as necessary using control signals Vtrim to trim the resistance in the ladder, which essentially sets threshold Vt2.

Figure 3B:
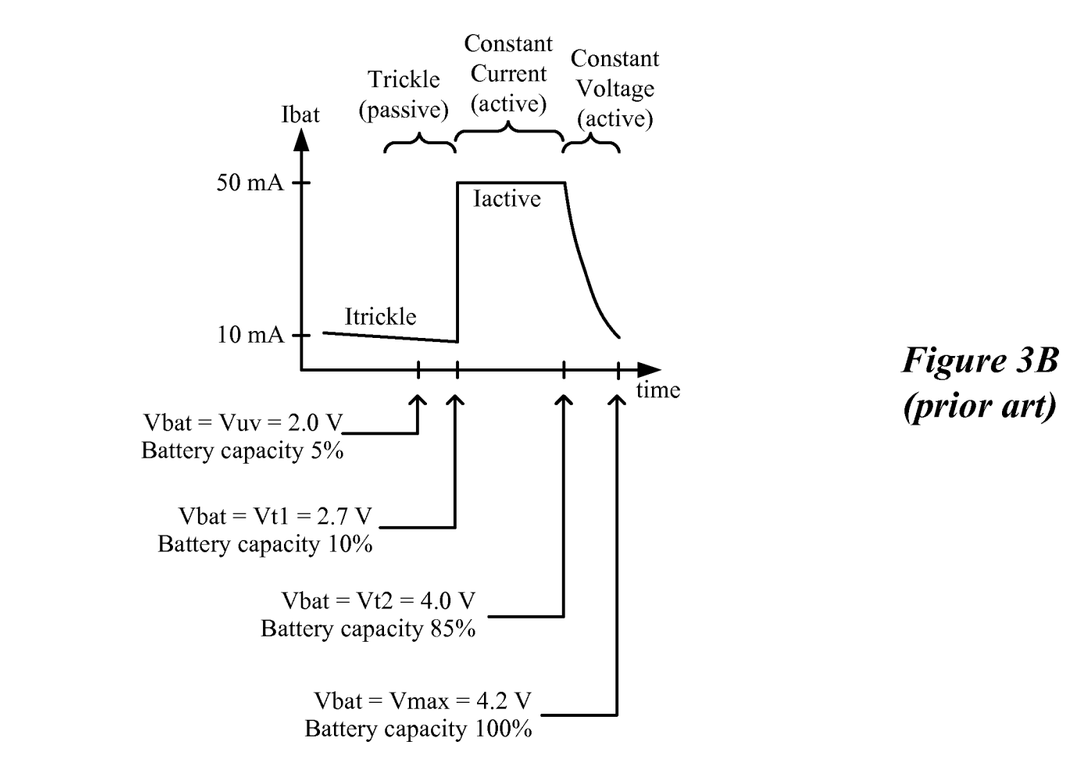
FIG. 3B shows a graph of the battery charging current provided by both the trickle and active charging paths as a function of time, in accordance with the prior art.

FIG. 3B generally illustrates operation of the charging circuitry 80 to produce the charging current (Ibat) received by a severely depleted battery 36 (i.e., where Vbat is below an even lower threshold V(UV)=2.0V) as a function of time during a charging session, including the trickle, constant current, and constant voltage modes enabled by the charging circuitry 80 as described above. Also shown are typical values for the charging current in each of these modes, and the capacity of the battery 36 illustrated as a percentage.

The battery management circuitry 84 of FIG. 2 provides additional safeguards as discussed in the '943 Publication. For example, diode(s) 54, preferably matching diode(s) 52 in number, are connected between the trickle and active charging paths, which ensure that both the source and drain of the overvoltage switch 60 are biased to the same voltage—to Vbat—even when Vbat is low. Diode(s) 54 thus protect the battery 36 from inadvertently discharging through overvoltage switch 60, particularly at the inopportune time when Vbat is already critically low, and when it therefore might be difficult to provide a suitably high voltage to the gate of P-channel transistor 60 to turn it off.

The problem of low levels for Vbat is significant. If Vbat is severely depleted, i.e., if Vbat<V(UV)=2.0V for example, it may be difficult to recover (recharge) the battery 36 by traditional trickle charging techniques. This is because, as mentioned earlier, rechargeable batteries are unable to handle large charging currents without damage, and Itrickle, as passively set by the resistance R of the components (50, 52) in the trickle charging path, may be too large when Vbat<V(UV). In fact, the inventors note that the trickle charging path of the '943 Publication exacerbates this problem: while the magnitude of Itrickle should ideally scale with the magnitude of Vbat (i.e., with Itrickle decreasing as Vbat decreases) to prevent battery damage, the opposite of this ideal occurs. This is because Itrickle=(Vdc−Vbat)/R, and thus Itrickle increases as Vbat decreases, as shown in FIG. 3B. This behavior of Itrickle is contrary to what is desired to safely recharge a severely depleted battery.

Additionally, the magnitude of Itrickle is difficult to control in any event, because it will vary as Vdc varies. Vdc varies in accordance with the coupling between the charging coil 92 in the external charger 90 and the charging coil 44 in the IPG 10, which coupling is affected by distance, axial offset, and angular offset between the coils. See, e.g., U.S. Patent Application Publication 2013/0096651. Because different patients will have IPGs implanted at different depths and angles, Vdc will be different between patients; for example, patients having shallow (well-coupled) implants could register a higher Vdc than would patients having deep (poorly-coupled) implants. Moreover, Vdc will also vary from time to time for a given patient, as the patient may not always position the external charger 90 in exactly the same place relative to the IPG 10 during different charging sessions, or because this positioning may shift during a charging session. Any of these effects can cause Vdc to vary, typically from 2.5 to 5.5V. Such Vdc variations mean that Itrickle may be too low to be significant in one circumstance, or too high in another circumstance, exacerbating battery reliability concerns.

The inventors thus notice problems using passive trickle charging to charge an implantable medical device battery, particularly at low battery voltages, and provide new techniques.

BRIEF DESCRIPTION OF THE DRAWINGS

FIG. 3A shows circuitry for a current/voltage source in the active current path, while

DETAILED DESCRIPTION

Improved charging circuitry for charging a battery in an Implantable Medical Device (IMD) such as an IPG is disclosed. The charging circuitry includes a source capable of producing a constant charging current via a current mirror that receives a reference current for setting the charging current. Two reference current generators are provided. The first reference current generator is powered by Vdc (the voltage produced by the front-end circuitry upon receipt of a magnetic charging field), and is enabled when Vbat is severely depleted to produce a small non-adjustable reference current of a stable magnitude that is independent of the Vdc power supply. This allows the current mirror to produce a small charging current also independent of Vdc and considerate of the battery's depleted state, even though the low value of Vbat is too low to reliably control the charging circuitry generally. The second reference current generator is enabled to produce a reference current once the battery voltage is suitably recovered. The magnitude of the reference current produced by the second reference current generator, and hence the resulting charging current, can be adjusted by control signals, which control signals are now reliable given the rise in Vbat. A passively-generated undervoltage control signal is used to enable and disable use of the first and second reference current generators. Through use of this improved charging circuitry, the battery can be charged without the need for a passive trickle charging path, even if the battery is severely depleted.

As noted, the inventors notice problems with passive trickle charging circuitry as used the prior art of FIG. 2. Given the ability to program the current/voltage source 56 (via Itrim control signals) to set the magnitude of Iactive in the active charging path, the inventors considered simply removing the trickle charging path from the charging circuitry 80, and programming the source 56 to provide significantly smaller charging currents when the battery 36 is significantly depleted (e.g., below Vt1=2.7V). In effect, this comprises enabling the source 56 to operate at these lower voltages for Vbat to provide small charging currents generally mimicking charging current magnitudes provided by Itrickle (e.g., 10 milliamps).

However, the charging circuitry 80 used in the prior art active charging path may not function well at low levels for Vbat, particularly if the battery 36 is severely depleted (Vbat<V(UV)=2.0). This is because Vbat generally also provides the power supply for the charging circuitry 80. For example, and as shown in FIG. 3A, the amplifier 112 in the Vbat measurement circuitry 111 is powered by Vbat. The reference current generator 113 is also ultimately reliant on and powered by Vbat, in particular because the system reference current I' is generated using Vbat. The control signals (Itrim, Vtrim, Ch_en) are also dependent on Vbat, because the microprocessor 110 and the source controller 86 are also powered by Vbat. Thus, the analog circuitry in the source 56 and the digital control signals may not operate reliably when Vbat is severely depleted. This hampers use of the source 56 at these lower battery voltages to provide needed small charging currents.

Figure 4:
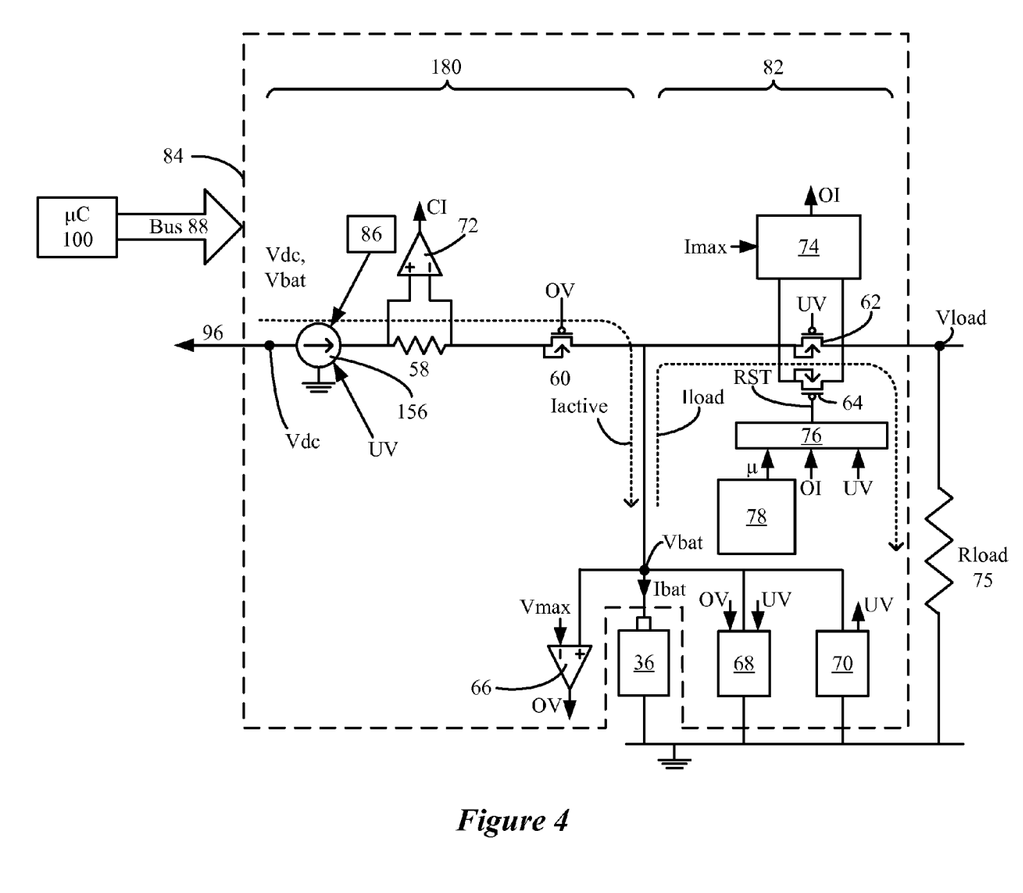
FIG. 4 shows improved battery management circuitry, and in particular improved charging circuitry which doesn't include a trickle charging path, but includes improved source circuitry in the active charging path.

FIG. 4 shows improved charging circuitry 180 for an implantable medical device such as an IPG 10 having a rechargeable battery 36. Many of the components in the battery management circuitry 84 as depicted in FIG. 4 are unchanged from the '943 Publication discussed earlier and shown in FIG. 2, and are thus not described again. For example, the load isolation circuitry 82 can remain unchanged and operate as before. Some components (the external charger 90; the front-end charging circuitry 96) have been removed in FIG. 4 for easier viewing.

Several differences exist in the improved charging circuitry 180. First, the trickle charging path is absent, and the active charging path includes improved current/voltage source circuitry 156 that is used exclusively to charge the battery 36, even when the battery is severely depleted. Notice that removal of the trickle charging path simplifies the charging circuitry 180, including removal of the diode(s) 54 previously connected between the trickle and active charging paths (FIG. 2). While removing the trickle charging path is preferable to remove the problems identified earlier, it could still be used in charging circuitry 180, but perhaps passively set (by resistor 50, diode(s) 52; FIG. 2) to provide very small currents on the order of a milliamp to guarantee only a very small Itrickle that would not damage the battery 36, even if Vbat was severely depleted down to a level approaching zero Volts.

Second, the source 156 receives an undervoltage control signal, UV, as an input. For convenience, this control signal UV can be the same as issued by the undervoltage detection circuitry 70 used to control connection of the battery 36 to the load 75 via switches 62 and 64 in the load isolation circuitry 82 as described earlier. However, control signal UV can be supplied to the source 156 from a different undervoltage detector (not shown), perhaps set to trigger at a different threshold voltage than undervoltage detector 70 (V(UV)=2.0V).

Figure 5A:
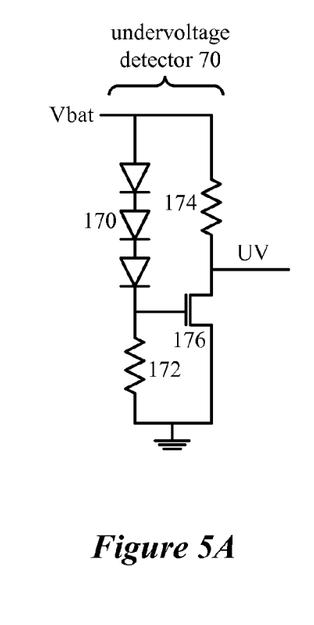
FIG. 5A shows circuitry for detecting an undervoltage condition used by the improved source circuitry.

Circuitry for the undervoltage detector 70 as disclosed in the '943 Publication is shown in FIG. 5A. Note that the undervoltage detector 70 does not receive and is not controlled by control signals, and thus passively outputs control signal UV, which is preferred because this circuit must work reliably at low levels for Vbat when control signals may not be trustworthy. When Vbat>V(UV)=2.0V, the voltage divider formed by diodes 170 and resistor 172 forms a suitably high voltage at the gate of N-channel transistor 176 to turn it on, which pulls UV to '0'. By contrast, when Vbat<V(UV)=2.0V, the voltage at the gate of transistor 176 is not high enough to turn on that transistor. UV is thus pulled to '1' (i.e., to Vbat) through a pull-up resistor 174. Both of resistors 172 and 174 are in the range of tens of MegaOhms. The forward drop across the diode(s) 170 (as well as their number) and the resistor 172 thus effectively operate to set the value of threshold V(UV). Although not shown, control signal UV may be buffered at the output of the undervoltage detector 70 to improve its integrity.

Figure 5B:
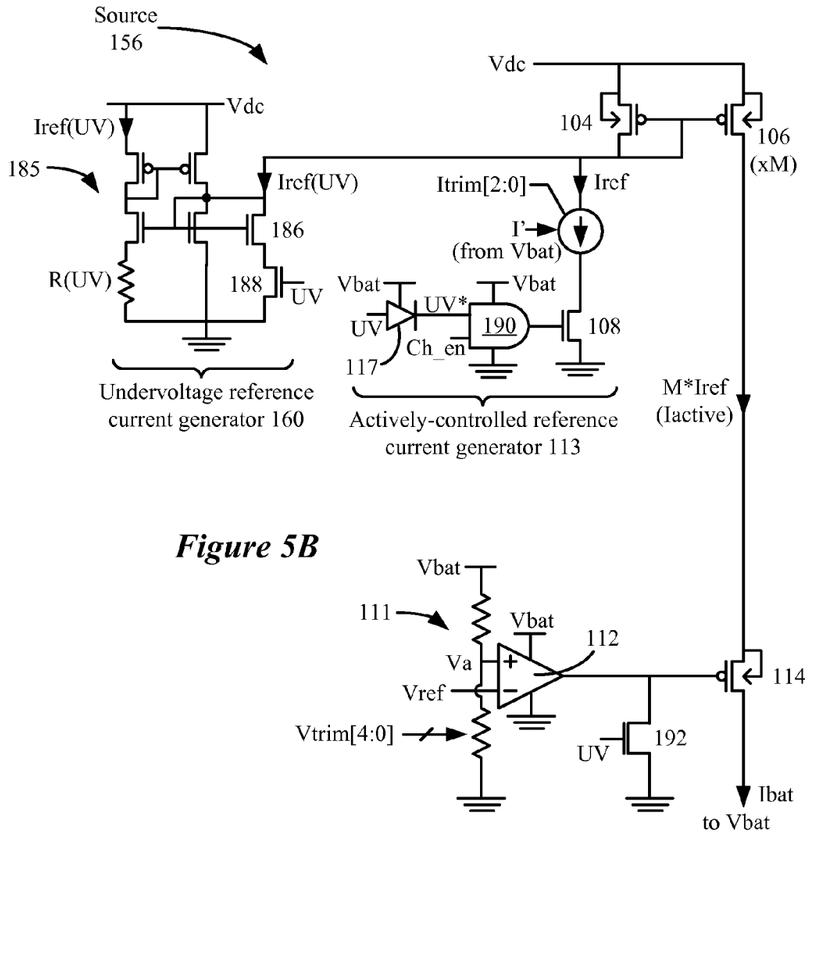
FIG. 5B shows the improved source circuitry, including an undervoltage reference current generator powered by Vdc during an undervoltage condition, which allows for generation of a small stable charging current, and a reference current generator powered by Vbat when the undervoltage condition is not asserted, which allows for generation of a charging current in accordance with control signals, in accordance with an aspect of the invention.

Changes to the current/voltage source circuitry 156 are shown in FIG. 5B. The actively-controlled reference current generator 113 remains largely as described earlier with respect to FIG. 2, and is again controlled by control signals Itrim to adjust Iref, and hence Iactive. However, and as explained further below, actively-controlled reference current generator 113 is only enabled and used to provide Iref to the current mirror transistors 104 and 106 when Vbat>V(UV)=2.0V. This is desired given actively-controlled reference current generator 113 being powered by Vbat (particularly as reflected in system reference current I'), as well as its general dependence on Vbat (as reflected in its reliance on the Itrim control signals ultimately generated by Vbat), which may cause generator 113 to function unreliably at low levels of Vbat. Note that an AND gate 190 has been added to control the gate of reference current enable transistor 108, as will be explained further below.

An additional undervoltage reference current generator 160 is newly provided in the source 156 to provide a small second reference current, Iref(UV), to the current mirror transistors 104 and 106, but is only enabled when Vbat<V(UV)=2.0V. The undervoltage reference current generator 160 includes a current source 185 to produce Iref(UV). However, current source 185 is not dependent on or powered by Vbat, but is instead powered by Vdc.

Current source 185, of conventional design, produces Iref(UV) with a magnitude that is relatively independent of the magnitude of its power supply voltage, Vdc, which is desired because as noted earlier, Vdc can vary. See, e.g., U.S. Pat. No. 6,737,909 (discussing the circuitry of current source 185 and its independence on power supply voltage). The magnitude of Iref(UV) is set in current source 185 by a resistor, R(UV), as well as by the sizing of its various transistors, without the use of actively-generated control signals, which may be unreliable at low voltages. Note that Iref(UV) is mirrored by transistor 186 which provides Iref(UV) to current mirror transistors 104 and 106. Iref(UV) is set to produce via current mirror transistors 104 and 106 an Iactive of a small magnitude that won't damage even a severely depleted battery 36, for example, on the order of a milliamp. As explained further below, Iref(UV) is preferably smaller than Iref.

As discussed earlier, control signal UV and/or its complement UV* as generated by an inverter 117 is/are provided to the source 156 to enable and disable the generators 160 and 113 in a mutually exclusive fashion, dependent on the magnitude of Vbat.

Specifically, UV is provided to a gate of an enable transistor 188 in the undervoltage reference current generator 160, which only allows Iref(UV) to be provided through transistor 186 to current mirror transistors 104 and 106 when Vbat<V(UV) (UV='1'). When Vbat>V(UV) (UV='0'), enable transistor 188 is off and generator 160 is disabled from producing Iref(UV), and thus disabled from contributing to the battery charging current.

Control signal UV* is provided to AND gate 190 in the actively-controlled reference current generator 113, along with the charge enable control signal, Ch_en, issued by the source controller 86, and thus both of these control signals must be set to '1' to turn on enable transistor 108 to allow Iref to be produced. Thus, reference current generator 113 is only enabled if Vbat is high enough (Vbat>V(UV); UV='0') and if source controller 86 (and ultimately the microcontroller 100) confirm that generator 113 should operate. When Vbat<V(UV) (UV='1'), enable transistor 108 is off and generator 113 is disabled from producing Iref, and thus disabled from contributing to the battery charging current.

Pull down transistor 192 in the Vbat measurement circuitry 111 is gated by UV, and so when Vbat<V(UV) (UV='1'), the gate of P-channel transistor 114 is pulled to '0' to turn this transistor on. In effect, the amplifier 112 is effectively disabled in this mode, as its output will be masked by transistor 192 pulling this output to ground. When Vbat>V(UV) (UV='0'), pull down transistor 192 is off, and amplifier 112 can operate to measure Vbat and control transistor 114 in the active charging path to effect the transition from constant current to constant voltage charging.

It should be noted that the disclosed circuitry for enabling and disabling generators 160 and 113 and measurement circuitry 111 as a function of Vbat are merely examples, and other circuitry could be used.

With this explanation of the improved source circuitry 156 in hand, its operation can now be discussed and appreciated. When Vbat is severely depleted, i.e., when Vbat<V(UV)=2.0V, the source 156 enables the undervoltage reference current generator 160 via passively-generated control signal UV='1' to produce a non-adjustable small reference current, Iref(UV), and hence to generate a small non-adjustable charging current Iactive to charge the battery 36. The actively-controlled reference current generator 113 and Vbat measurement circuitry 111 are disabled in this mode, as described above. Notice in this mode, operation of source 156 occurs without actively-generated control signals. The states of control signals Itrim, Vtrim, and Ch_en are irrelevant because circuits in the source 156 receiving such control signals are effectively disabled.

When generator 160 has charged the battery 36 to the point where it is no longer severely depleted, i.e., when Vbat>V(UV)=2.0V (UV='0'), the undervoltage reference current generator 160 is disabled, and the actively-controlled reference current generator 113 is enabled. Thus, the charging current Iactive can be adjusted (and increased) via adjusting Iref with the Itrim control signals, which are now reliably produced given the increase in Vbat. Vbat measurement circuitry 111 is also enabled and reliably controllable, and thus can function to transition the source 156 from constant current charging to constant voltage charging (i.e., when Vbat passes Vt2), in the manner explained earlier. In effect, in this mode, the source 156 acts similarly to the source 56 of FIG. 2.

Figure 5C:
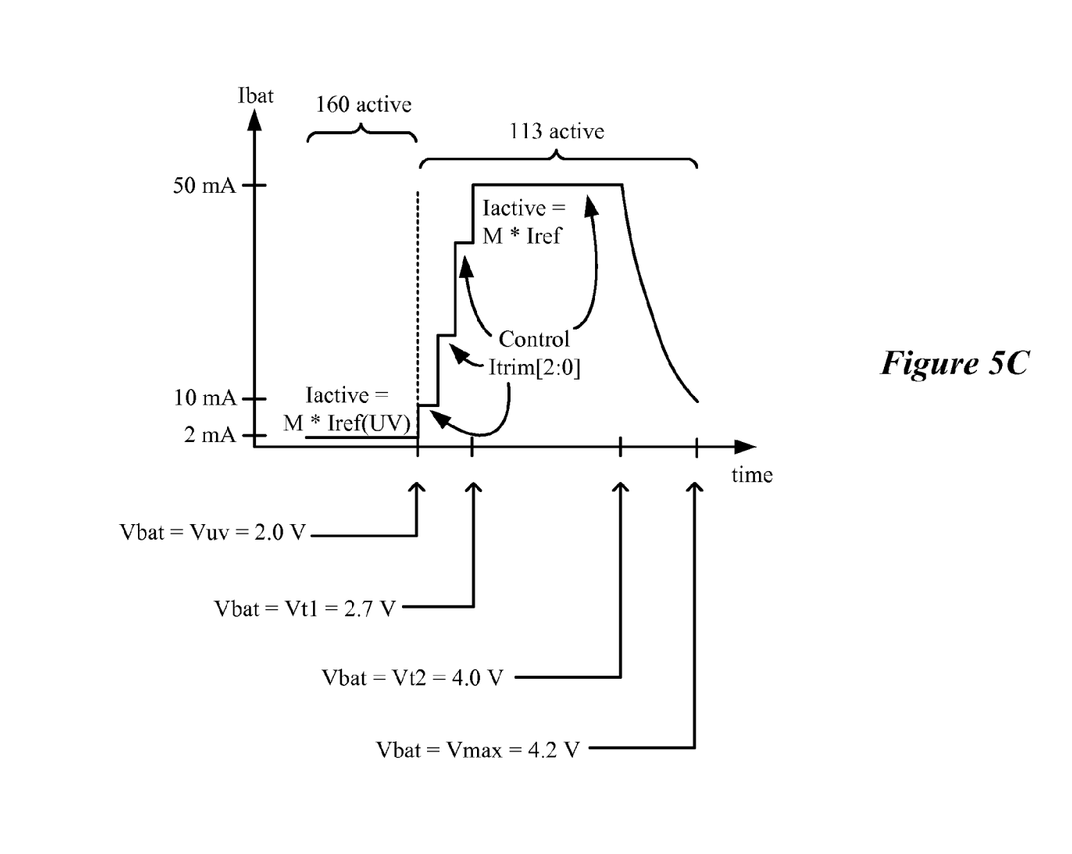
FIG. 5C shows a graph of the battery charging current provided using the improved charging circuitry as a function of time, in accordance with an aspect of the invention.

FIG. 5C generally illustrates operation of the improved charging circuitry 180 to produce the battery charging current Ibat received by a severely depleted battery 36 (i.e., where Vbat<V(UV)=2.0V), similar to what was illustrated earlier in FIG. 3B for the prior art. When Vbat<V(UV), a small non-adjustable charging current (Iactive=M*Iref(UV)) is produced by the source 156. Not only is this charging current sufficiently small to prevent damage to the severely depleted battery 36, it is also held constant by virtue of the constant, non-power-supply-dependent value of Iref(UV) provided by current source 185 in undervoltage reference current generator 160. Note that providing a constant charging current at such low values for Vbat is much preferred compared to operation of the trickle charge path used in the prior art, which as noted earlier undesirably produced higher trickle currents at lower values for Vbat.

Once Vbat reaches V(UV)=2.0 and is no longer severely depleted, the actively-controlled reference current generator 113 is enabled, because reliable operation of the source 156 and its actively-generated control signals can be assumed given the increase in Vbat. Note however that the battery 36 is still significantly depleted at this point (<Vt1=2.7V), and therefore it may not be advisable to set the now-enabled actively-controlled reference current generator 113 to provide a maximum value for Iref per the Itrim control signals. Thus, as shown, the Itrim control signals are preferably asserted to gradually increase Iref, and hence Iactive=M*Iref, until the battery 36 is no longer significantly depleted (i.e., when Vbat>Vt1=2.7V), at which point Iref may be set by Itrim to a high or maximum limit. However, battery charging current M*Iref ultimately produced by the actively-controlled reference current generator 113 is preferably larger than M*Iref(UV) produced by the undervoltage reference current generator 160, even if M*Iref is gradually increased. As before, constant current charging can continue at these levels until Vbat=Vt2=4.0, when constant voltage charging commences and continues until charging of the battery 36 is complete (at Vbat=Vmax=4.2).

As the improved charging circuitry 180 lacks diode(s) 54 (FIG. 2) used to prevent leakage through the overvoltage switch 60 as described earlier, other measures can be taken to address this concern. For example, U.S. Pat. No. 6,020,778 discloses circuitry for a transmission gate that can be used for overvoltage switch 60 including both a P-channel pass transistor and an N-channel pass transistor. Further disclosed in the '778 patent is circuitry for biasing the well of the P-channel pass transistor to the highest of the voltages on either side of the transmission gate, and for biasing the well of the N-channel pass transistor to the lower of these voltages.

While control of the source 156 has been disclosed as occurring via a microcontroller 100 and a source controller 86, such means of dividing control is not strictly necessary. Instead, control circuitry for the charging circuitry 180 could instead be integrated in other IMD designs, such as on a single integrated circuit. The charging circuitry 180 itself may also be integrated with such control circuitry, such as in the ASIC described earlier.

The disclosed technique can be used in conjunction with the battery charging technique disclosed in U.S. provisional patent application 61/928,352 referenced above, in which the battery charging current is adjusted over the life of the IMD in accordance with historical parameters having relevance to battery capacity.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Battery charging circuitry for a medical device, comprising:
    a rechargeable battery having a battery voltage and configured to receive a battery charging current;
    front-end circuitry configured to generate a DC voltage upon receipt of a wireless charging field;
    undervoltage detection circuitry configured to indicate whether the battery voltage is above or below a threshold voltage; and
    source circuitry controllable to produce
        a first constant battery charging current as the battery charging current along an active charging path from the source circuitry to the battery when the undervoltage detection circuitry indicates that the battery voltage is below the threshold voltage, and
        a second constant battery charging current as the battery charging current along the active charging path from the source circuitry to the battery when the undervoltage detection circuitry indicates that the battery voltage is higher than the threshold voltage, wherein the first constant battery charging current is smaller than the second constant battery charging current,
    wherein the source circuitry comprises a current mirror configured to produce the battery charging current from a reference current, and
    wherein the source circuitry further comprises a first reference current generator and a second reference current generator, wherein the first and second reference current generators are configured to be enabled mutually exclusively to provide the reference current.

2. The circuit of claim 1, wherein the current mirror is powered by the DC voltage.

3. The circuitry of claim 1, wherein the first reference current generator is enabled when the undervoltage detection circuitry indicates that the battery voltage is below the threshold voltage, and wherein the second reference current generator is enabled when the undervoltage detection circuitry indicates that the battery voltage is higher than the threshold voltage.

4. The circuitry of claim 1, wherein a magnitude of the first constant battery charging current is independent of a magnitude of the DC voltage.

5. The circuitry of claim 1, wherein a magnitude of the first constant battery charging current is not adjustable.

6. The circuitry of claim 1, wherein a magnitude of the second constant battery charging current is adjustable in accordance with one or more control signals.

7. The circuitry of claim 1, wherein the front-end circuitry comprises a coil configured to be energized by the wireless charging field, and rectifier circuitry configured to produce the DC voltage from the energized coil.

8. The circuitry of claim 1, wherein the undervoltage detection circuitry is not controlled by a control signal, and thus is configured to passively indicate whether the battery voltage is above or below the threshold voltage.

9. The circuitry of claim 1, wherein the undervoltage detection circuitry issues an undervoltage control signal to the source circuitry, wherein undervoltage the control signal indicates whether the battery voltage is above or below a threshold voltage.

10. The circuitry of claim 1, further comprising a switch configured to pass the battery charging current to the battery, wherein the switch is controlled by battery voltage measurement circuitry.

11. The circuitry of claim 10, wherein the switch is controllable in accordance with the battery voltage.

12. Battery charging circuitry for medical device, comprising:
    a rechargeable battery having a battery voltage and configured to receive a battery charging current;
    front-end circuitry configured to generate a DC voltage upon receipt of a wireless charging field;
    undervoltage detection circuitry configured to indicate whether the battery voltage is above or below a threshold voltage; and
    source circuitry configured to produce the battery charging current from a reference current, the source circuitry comprising
        a first reference current generator configured to produce a first reference current as the reference current when the undervoltage detection circuitry indicates that the battery voltage is below the threshold voltage, and
        a second reference current generator configured to produce a second reference current as the reference current when the undervoltage detection circuitry indicates that the battery voltage is higher than the threshold voltage,
    wherein the first and second reference current generators are configured to be enabled mutually exclusively to provide the reference current.

13. The circuitry of claim 12, wherein the source circuitry comprises a current mirror configured to produce the battery charging current from the reference current.

14. The circuit of claim 13, wherein the current mirror is powered by the DC voltage.

15. The circuitry of claim 12, wherein the first reference current generator is powered by the DC voltage.

16. The circuitry of claim 15, wherein a magnitude of the first reference current is independent of a magnitude of the DC voltage.

17. The circuitry of claim 12, wherein a magnitude of the first reference current is not adjustable and is set by the first reference current generator.

18. The circuitry of claim 12, wherein the second reference current generator is powered by the battery voltage.

19. The circuitry of claim 12, wherein a magnitude of the second reference current is adjustable in accordance with one or more control signals.

20. The circuitry of claim 12, wherein the first reference current is smaller than the second reference current.

21. The circuitry of claim 12, wherein the front-end circuitry comprises a coil configured to be energized by the wireless charging field, and rectifier circuitry configured to produce the DC voltage from the energized coil.

22. The circuitry of claim 12, wherein the undervoltage detection circuitry is not controlled by a control signal, and thus is configured to passively indicate whether the battery voltage is above or below the threshold voltage.

23. The circuitry of claim 12, wherein the undervoltage detection circuitry issues an undervoltage control signal to the first and second reference current generators, wherein undervoltage the control signal indicates whether the battery voltage is above or below a threshold voltage.

24. The circuitry of claim 12, further comprising a switch configured to pass the battery charging current to the battery, wherein the switch is controlled by battery voltage measurement circuitry.

25. The circuitry of claim 24, wherein the switch is controllable in accordance with the battery voltage.

* * * * *